United States Patent [19]
Eibl et al.

[11] Patent Number: 5,833,984
[45] Date of Patent: Nov. 10, 1998

[54] COMPOSITION AND METHOD FOR PREVENTING AND TREATING INFLAMMATION WITH IMMUNOGLOBULIN A

[75] Inventors: Martha Eibl; Hermann Wolf; Josef W. Mannhalter; Heinz Leibl; Yendra Linnau, all of Vienna, Austria

[73] Assignee: Immuno Aktiengesellschaft, Vienna, Austria

[21] Appl. No.: 772,264

[22] Filed: Dec. 23, 1996

Related U.S. Application Data

[63] Continuation of Ser. No. 198,067, Feb. 18, 1994, abandoned.

[51] Int. Cl.$^6$ .......................... A61K 39/395; C07K 16/06
[52] U.S. Cl. ..................... 424/130.1; 424/184.1; 530/387.1; 530/861; 530/868
[58] Field of Search .............................. 424/130.1, 184.1; 530/387.1, 861, 868

[56] References Cited

U.S. PATENT DOCUMENTS 4,335,099  6/1982  Funakoshi et al. .

FOREIGN PATENT DOCUMENTS

| | | |
|---|---|---|
| 0479597A2 | 4/1992 | European Pat. Off. . |
| 56-53622 | 5/1981 | Japan . |
| 57-59815 | 4/1982 | Japan . |

OTHER PUBLICATIONS

EiBL et al., *Journal of Clinical Immunology*, vol. 10, No. 6 (Nov. Supp. 1990) pp. 725–795.
Peeters et al. *Annals of the Rheumatic Diseases*, vol. 49. pp. 636–640.
Takei et al. *J. Clin. Invest.*, vol. 91, pp. 602–607 (Feb. 1993).
Boyum, *The Scandinavian Journal of Clinical & Laboratory Investigation*, vol. 21, Suppl 97, pp. 77–89 (1968).
Kabat et al., *Experimental Immunochemistry*, Second Edition, Fourth Printing, pp. 133–157 (Jan. 1971).
Male, et al., Advanced Immunology, J.B.Lippincott Co., Philadelphia, pp. 16, 18, 1990.
The Sigma ImmunoChemicals Catalog, 1990, pp. 181–182.
Barron et al., J. Rhematology, 1992, 19(Suppl 33):94.
Physicians Desk Reference, 1990, Sandoz Product Information.

*Primary Examiner*—Frank C. Eisenschenk
*Attorney, Agent, or Firm*—Foley & Lardner

[57] ABSTRACT

Inflammation can be treated or prevented altogether by administering a preparation comprising IgA. These preparations also can effect immunomodulation. Preferably, the preparation includes multimeric IgA and is essentially free of IgG in its various forms. Other compounds, such as antibiotics, antiphlogistic agents and antacids, also may be administered. Immunoglobulin A may also be used in vaccines to prevent inflammation. Additionally, an improved assay for evaluating anti-inflammatory activity is provided.

14 Claims, 7 Drawing Sheets

COMPOSITION AND METHOD FOR PREVENTING AND TREATING INFLAMMATION WITH IMMUNOGLOBULIN A

This application is a continuation of application Ser. No. 08/198,067, filed Feb. 18, 1994 now abandoned.

BACKGROUND OF THE INVENTION

The present invention relates to a method for the prevention or treatment of inflammatory reactions, both acute and chronic, by administering a pharmaceutical preparation containing immunoglobulin A ("IgA"). The invention also relates to using a pharmaceutical preparation containing multimeric IgA for treating, averting or ameliorating such inflammatory reactions, even in the course of vaccination. The invention further relates to an in vitro test for evaluating the anti-inflammatory and immunomodulating activity of a substance.

Deleterious inflammatory events can occur throughout the body. For instance, events at mucosal surfaces, such as inflammation of the upper respiratory tract and stomatitis aphtosa, can occur. Inflammatory events can also occur throughout the respiratory tract as well as the gastrointestinal tract. Some mucosal inflammatory events are not directly mediated by an infectious agent, but rather result from overreaction of the immune system in response to microbial infection. Illustrative maladies are acute obstructive bronchitis and respiratory tract infections exacerbated by asthma.

Deleterious inflammation can occur at locations other than mucosal surfaces. Diseases at such non-mucosal sites include rheumatoid arthritis (systemic juvenile rheumatoid arthritis and psoriatic arthritis), Reiter's syndrome, ankylosing spondylitis, Crohn's and Whipple's disease with arthritis, and systemic lupus erythematosus.

Deleterious inflammation generally is the result of uncontrolled reactions in the immune system. Certain antigens play a role in the inflammation process and cause damage by virtue of this role. For instance, the majority of toxic effects of systemic gram-negative infection and endotoxemia are mediated through interaction with cells of the immune system, especially the macrophage. Cells of the monocyte/macrophage lineage are the principal source of inflammatory cytokines such as tumor necrosis factor-alpha ("TNF-$\alpha$") and interleukin 6 ("IL-6").

The inflammatory cytokines are produced in response to a variety of biological stimuli, such as lipopolysaccharide ("LPS") from gram negative bacteria. TNF-$\alpha$ and IL-6 play a central role in multiple effector functions and cellular interactions necessary to mount an effective host defense during inflammation and immune response. However, uncontrolled production of inflammatory cytokines is damaging to the host. For example, uncontrolled, LPS-induced release of TNF-$\alpha$ has been shown to be a central mediator of LPS-induced toxicity, including gram-negative endotoxic shock.

The injection of high doses of TNF-$\alpha$ into rats or mice induces the symptoms and lethality of septic shock. Furthermore, high serum levels of TNF-$\alpha$ correlate with the mortality of patients with meningococcemia or septic shock. High levels of TNF-$\alpha$ have also been found in neonates with necrotizing enterocolitis, suggesting that TNF-$\alpha$ may be involved in the pathogenesis of this disease. Indeed, endotoxin challenge and administration of TNF-$\alpha$ has induced bowel necrosis in an experimental model of neonatal necrotizing enterocolitis. Increased levels of IL-6 are found in a variety of clinical conditions including bacterial and viral meningitis and HIV infection. Endotoxins are known to induce IL-6 synthesis, and serum levels of IL-6 are increased in conditions associated with endotoxemia such as thermal injury. The deleterious effects of bacterial toxins are associated with the exaggerated and self-amplifying release of these compounds that cause inflammation, often with lethal results. The lethality of gram-negative bacteremia or endotoxemia has been prevented by the administration of specific, anti-TNF antibodies.

The various components of the immune system are implicated in inflammatory phenomena. One of the major components of the immune system are the immunoglobulins. Pharmaceutical preparations containing immunoglobulins have been previously used in the prophylaxis and treatment of bacterial and viral infections. For instance, in U.S. Pat. No. 4,335,099 an oral preparation containing IgA and immunoglobulin G ("IgG") was used for the treatment of intestinal infections. Additionally, preparations containing 73% IgA and 26% IgG, in terms of total immunoglobulin content, are capable of reducing the incidence of necrotizing enterocolitis when prophylactically administered to low birthweight infants. See Eibl et al., *J. Clin. Imm.* 10(6): 72S-79S (1990). This effect is believed to be a result of the formation of antigen-antibody complexes caused by the high titers of antibodies against a multitude of potential pathogens and their toxins. Such pathogens include bacterial agents causing pertussis, tetanus and diphtheria and viruses such as poliovirus, Coxsackie virus, rotavirus, and echovirus.

IgA, IgG and transferrin have been shown to act synergistically against bacterial growth (see EP 0 506 651). The proportions of the active components are between 0.40 and 0.80 parts by weight of IgG and 0.15 to 0.45 parts by weight of transferrin per part by weight of IgA.

IgG, IgA and IgM have been shown to act synergistically with other pharmacologically active compounds, such as antibiotics. These immunoglobulins presumably bind to infective microorganisms, which results in agglutination or induction of phagocytosis. See EP 0 168 830.

It is well known, therefore, that immunoglobulins can be useful because a specific antibody recognizes and binds to a specific antigen to neutralize that antigen.

However, it has been thought that certain immune complexes may play a role in certain inflammatory processes. For example, there have been reported findings of IgA-immune complexes in patients suffering from inflammatory bowel disease and ankylosing spondylitis. The patients suffering from these disease had high concentrations of serum IgA and circulating IgA immune complexes. See Peeters et al., *Ann Rheumat. Dis.* 49: 638–640 (1990).

Preparations containing certain IgG antibodies have been found to protect against systemic disease caused by staphylococcal infection by inhibiting T-cell activation induced by bacterial toxins (superantigens). See Takei et al., *J. Clin. Invest.* 91: 602–607 (1993). This protective effect of IgG preparations can be attenuated by neutralizing antibodies. The effect of these antibodies probably occurs through inhibition of T-cell activation by the bacterial superantigen, which could otherwise lead to propagation and enhancement of a systemic inflammatory reaction. Thus, according to the anti-superantigen hypothesis the use of certain IgG antibodies against various immunological diseases, other than antibody deficiency disorders, may be feasible. See Rich, *J. Clin. Invest.* 91: 378 (1993).

The other predominant immunoglobulin, IgA, also plays an important role in the immune system. For example, secretory IgA ("SIgA") plays a major role in the protection of the host from infection by pathogenic organisms invading via the mucosal surfaces of the respiratory, gastrointestinal and urogenital tracts. IgA antibodies participate in the clearance of pathogenic bacterial, viral or parasitic organisms and a variety of ingested or inhaled antigens from the mucosal surfaces by neutralizing toxins and viral particles, inhibiting adherence of bacterial pathogens, and preventing colonization and penetration of mucosal surfaces by pathogenic micro-organisms.

The anti-infectious effects of preparations containing IgA that is practically free of IgG are disclosed by Japanese patent publications Sho 56-53622 and Sho 57-59815. These preparations contained 92% IgA and 6% IgG. These preparations decreased the mortality caused by *Pseudomonas aeruginosa* in mice. These preparations contain monomeric IgA and have been shown to have a neutralizing effect on rotavirus, *Escherichia coli* and *Salmonella typhi*. Tests of various preparations showed that lower overall IgG content generally correlate with stronger anti-infectious effects.

Methods of obtaining IgA are known as well. For instance, a method for producing an immunoglobulin preparation comprising more than 10% IgA by ion-exchange chromatography is disclosed in DE 39 27 111 C2. Where the elution conditions are chosen to exclude IgM, a product containing 30–60% IgA and 70–40% IgG can be obtained. The anticomplementary activity of this preparation is relatively low.

Previous procedures for obtaining IgA from serum have focused on preventing polymerization of the immunoglobulin to avoid forming multimeric IgA. Polymerization of IgA is typically avoided even when isolating SIgA, which is actually dimeric. The monomer fraction of SIgA has previously been considered to be most valuable. A method for the production of a SIgA preparation is described by EP 0 479 597 A2.

Stabilizers have been used to obtain monomeric IgA yields of about 80%. Immunoglobulin polymers are then separated by fractional precipitation using polyethylene glycol. The avoidance of multimeric IgA in the prior art has limited the clinical use of IgA, however. This limited use is the result of the competing considerations of viral inactivation and avoidance of polymerization.

For example, an IgA preparation typically was heated to about 60° C. to inactivate contaminating viruses. This heating also causes immunoglobulin denaturation and subsequent polymerization to form IgA multimers. To avoid polymerization during viral inactivation, stabilizers were added to the immunoglobulin-containing solution. The stabilizers, however, also stabilize and thereby protect the contaminating viruses from inactivation.

SUMMARY OF THE INVENTION

It is an object of the present invention to provide a method for the treatment and prevention of acute and chronic inflammatory reactions in a subject, such as a human patient.

It is another object of the present invention to provide a method for the treatment and prevention of acute and chronic inflammatory reactions by administering IgA to a subject.

It is a further object of the present invention to provide a method for the treatment and prevention of acute and chronic inflammatory reactions by administering multimeric forms of IgA to a subject.

It is still another object of the present invention to provide a pharmaceutical preparation containing IgA, in its various forms, which is suitable for the prevention and treatment of inflammatory reactions.

It is still another object of the present invention to provide improved vaccination by administering IgA to minimize inflammation.

It is yet a further object of the present invention to provide an assay for screening anti-inflammatory compounds.

It is still a further object of the present invention to provide a preparation for modulating aspects of the immune response, such as the release of certain cytokines.

In achieving these and other objects, there is provided a method for preventing or treating inflammation, comprising the step of administering a preparation comprising IgA to a subject in need of such therapy. Preferably, the preparation includes multimeric IgA, and is essentially free of IgG. The preparation is also preferably free of viable infectious agents, such as viruses. Preferably, contaminating viruses are inactivated by heat treatment. Other compounds, such as antibiotics, antiphlogistic agents and antacids, may also be administered to the subject.

In accordance with another aspect of the present invention, there is provided a pharmaceutical preparation comprising multimeric IgA.

In accordance with another aspect of the present invention, there is provided a preparation comprising IgA. Preferably, the preparation includes multimeric IgA, and is essentially free of IgG. The preparation may also contain other compounds, such as antibiotics, antiphlogistic agents and antacids. One or more of these compounds may be part of an anti-inflammatory kit. The anti-inflammatory kit should contain instructions for the use of the preparation to prevent or treat inflammation. Instructions can include dosages and administration routes.

In accordance with still another aspect of the present invention, there is provided a method for evaluating anti-inflammatory activity of a test substance, comprising the steps of incubating cytokine-producing cells in a serum-free media in the presence of an inflammatory stimulus, such as antigens from inactivated bacteria (*Haemophilus influenzae*), and the test substance and evaluating the incubated cells for production of cytokines. Preferably, the cells are monocytes and the evaluated cytokines comprise TNF-$\alpha$, TNF-$\beta$, IL-1 or IL-6. Preferably, the results are compared to the cytokine production of a control, such as monocytes exposed to the inflammatory stimulus but not the test substance.

In accordance with yet another aspect of the present invention, there is provided a method for vaccination comprising administering IgA and an antigen. The administration may be simultaneous or sequential. Preferably, the IgA comprises multimeric IgA and the preparation is essentially free of IgG. An adjuvant may also be administered. One or more of these compounds may be part of a vaccination kit. The vaccination kit should contain instructions for the use of the preparation to prevent or treat inflammation before, during and after vaccination.

All components or preparations should be treated to eliminate or inactivate potentially-contaminating pathogenic microbes, such as blood-borne viruses. Other objects, features and advantages of the present invention will become apparent from the following description, tables and figures.

DETAILED DESCRIPTION OF THE INVENTION

In view of the consequences of deleterious inflammation, mechanisms are needed to down-regulate the local and systemic noxious sequelae associated with acute and chronic inflammation. The present invention employs advantageously a previously unknown property of IgA to prevent or treat deleterious inflammatory reactions. This property differs from the well-known model of antibody neutralization of specific foreign antigens. The existence of this property and usefulness of IgA as an anti-inflammatory were surprising in view of the findings of Peeters et al., loc. cit. and others.

The present invention thus relates to compositions and methodology for preventing or treating acute and chronic inflammatory reactions, such as generalized or localized inflammatory reactions, with an effective amount of IgA.

Immunoglobulin A can be administered prophylactically to subjects at risk for developing inflammation. Such subjects include those who are to be vaccinated as well as those who have been recently vaccinated or otherwise exposed to inflammatory stimuli or cytokines. The prophylactic use of IgA should thwart or minimize the onset of deleterious inflammatory reactions.

In the prophylactic context, subjects should receive IgA before exposure to the inflammatory stimulus or immediately after exposure thereto. For example, in the case of allergic diseases like rhinitis allergica, subjects should treated before exposure to allergens like pollen. Additionally, subjects at risk for infections of the upper respiratory tract with attendant inflammation should receive IgA repeatedly during the common cold season.

Immunoglobulin A can be also administered to subjects already suffering from deleterious inflammatory reactions. Inflammatory reactions can be encountered in subjects stung by bees or otherwise exposed to inflammatory stimuli. In this context, IgA should cure, ameliorate or minimize the ongoing inflammatory reactions.

The administration of IgA may be effected by local, oral or systemic routes. It is preferred to use IgA in a pharmaceutical preparation which is essentially free of IgG. It is also preferred to use a preparation containing multimeric IgA. The presence of IgM should also be minimized or eliminated altogether.

Dosages depend on the route and frequency of administration, as well as the extent and cause of the inflammation. Where high overall doses of IgA are to be administered, it is often preferred to administer the IgA in several smaller amounts over the course of the day. These dosage and administration route considerations are readily ascertained by the person skilled in the art.

For example, IgA can be administered orally (usually 1 to 10 g/day or more in severe cases), preferably in 3 or more doses given concomitantly with an antacid.

In addition, IgA can be administered systemically by means such as intravenous injections (by bolus, continuous infusion or both). Typically, 50 to 2000 mg IgA/kg/day are administered. In rare cases, intramuscular administration can be undertaken, usually at a dosage of about 50 to 100 mg IgA/kg/day.

Immunoglobulin A can also be administered locally by routes such as inhalation (up to 10 ml/day, 10 to 100 mg IgA/ml; nasally: 50 to 200 mg/ml by sprays or drops) or by intra-articular injection (as needed, 1–5 ml of 10 to 100 IgA/ml. Other routes include suppositories (100 to 1000 mg IgA/dose) and transdermal patches. Transdermal patches can be used to treat skin inflammations (psoriasis or acne).

Previously, the effects of IgA against pathogens have been considered to be mediated only by specific antibodies. For example, it was known that antibodies are involved in the inhibition of microbial attachment and the neutralization of bacterial toxins and viral particles. It was surprising, therefore, to discover a general anti-inflammatory and immunomodulating effect of IgA. Contrary to the existing hypothesis concerning the anti-superantigenic effects of certain IgG antibodies, IgG has no comparable effect to IgA when tested in parallel. Rather, IgG appears to actually enhance inflammatory activity, which is undesirable. Accordingly, it is preferred to use IgA which is essentially free of IgG.

According to the present invention, the prophylaxis and therapy of inflammatory reactions involves administering IgA to a subject in need. Such a subject would be one liable to inflammation or actually undergoing deleterious inflammatory events. An appropriate antibiotic and/or antiphlogistic may also be administered to such a subject. In some situations, and antacid may also be included. One or more of these components may be packaged as a together with appropriate instructions, which can indicate dosages and administration regimens. Preferably, each of the components are essentially free of IgG.

The phrase "essentially free of IgG" connotes a maximum of 20% IgG of the sum of immunoglobulins, preferably not more than 10% IgG. It is also preferred that the immunoglobulin fraction be practically free of IgM (not more than 5%, preferably not more than 3%). Accordingly, it is preferred to minimize or eliminate the presence of IgG and IgM in the practice of the present invention.

The methodology and corresponding kit of the present invention also are useful in combination with adjuvants.

Adjuvants are typically inactivated microorganisms or toxins which are used to enhance the immunological response to an antigen used in vaccination. The administration of IgA along with the adjuvant insures that undesirable inflammation induced by the adjuvant will be minimized or eliminated altogether.

A further aspect of the invention involves a pharmaceutical preparation containing at least 5%, preferably at least 10%, multimeric IgA. This preparation should be essentially free of polymeric IgG. "Essentially free of polymeric IgG" refers to maximum of 10% polymeric IgG of the sum of immunoglobulins. Preferably, the sum of immunoglobulins contains no more than 5% polymeric IgG. It also is preferred that the immunoglobulin preparation containing multimeric IgA is practically free of IgM.

The desirability of multimeric IgA is based on the surprising finding that even a low degree of IgA-polymerization (for example, by heat-aggregation) enhances the anti-inflammatory effect of IgA. This effect of multimeric IgA is unexpected in view of the well-known dangerous effects of polymeric IgG, which is responsible for nonspecific and excessive anticomplementary activity. A pharmaceutical preparation according to the present invention preferably comprises IgA as the main ingredient, which optionally is at least essentially free of IgG. It is preferred to minimize or eliminate the presence of IgG and IgM in their various forms.

The anti-inflammatory potency of a substance can be determined by means of a novel and reliable in vitro assay. The assay of the present invention involves the incubation of monocytes (a cytokine-producing cell) in a serum-free media in the presence of a substance to be tested. The monocytes are then exposed to an inflammatory stimulus, which typically would cause the monocytes to express inflammatory cytokines. The amount of the expressed cytokines, such as TNF-α, TNF-B, IL-1 and IL-6 is then determined. By comparing the amount expressed cytokines in the monocytes incubated with the test substance to a control, which is carried out in the absence of the test substance, an accurate indication of the anti-inflammatory activity of the substance being tested is obtained. Lymphocytes and granulocytes can also be used in this assay.

The inflammatory stimulus used in the assay of the present invention is preferably an inactivated bacterium, such as *Haemophilus influenza*, or a constituent thereof. Other suitable stimuli include *E. coli* LPS or meningococcal polysaccharide.

The novel assay described above has shown that IgA possess a general anti-inflammatory activity, which differs from the well-known model of antibody function. This anti-inflammatory activity can also be demonstrated by the inhibition of the oxygen radical release by monocytes and granulocytes. The release of these radicals in an inflammatory reaction leads to a significant damage of the tissue at the site of the inflammation. This phenomena is known as "respiratory burst," which can be measured by an in vitro model using Hib incubated in the presence of neutrophilic granulocytes. Anti-inflammatory activity can also be determined by inhibition of T-lymphocyte activation in response to a superantigen (such as staphylococcal enterotoxins, toxic shock syndrome toxin 1) and recall antigen (such as tetanus toxoid).

The anti-inflammatory effect of IgA is not solely based on the presence of specific neutralizing antibodies. This has been demonstrated by flow cytometric analysis using indirect immunofluorescence. This analysis shows that IgA and IgG preparations contain comparable titers of antibodies that bind Hib, but only IgA decreases the levels of TNF-α and IL-6 production. The IgG preparations examined at similar concentrations in parallel experiments have no down-regulating effect on Hib-induced cytokine release.

The non-reliance of IgA on specific neutralizing activity is further borne out in studies where IgA antibodies are incubated with Hib before the addition of the mixture to the monocytes. This incubation would allow formation of antigen-antibody complexes. However, the incubation of Hib with IgA does not enhance inhibition of inflammatory cytokine release.

According to the present invention, human serum IgA, which is largely monomeric, inhibits monocyte cytokine release. Heat aggregation, which forms IgA multimers, enhances the inhibitory effect of IgA on TNF-α release. A pharmaceutical preparation according to the present invention preferably contains multimeric IgA, which can be obtained by heating a preparation containing at least 80%, and more preferably at least 90%, IgA in solution or in the lyophilized form. The preparation should be essentially free of IgG and contain no detectable IgM. IgG and IgM can be detected by single radial immunodiffusion ("RID").

Preferably, a plasma fraction is used as a source of IgA. For example, an IgA fraction can be obtained by ion exchange chromatography, hydrophobic chromatography, hydrophilic chromatography or affinity chromatography of a plasma fraction, such as Cohn-fraction III. This process also assists in the reduction of a potential viral infectivity because viruses are inactivated and/or removed by Cohn-fractionation.

The heating may be carried out at 40° C. to 70° C., preferably at 60° C. to 65° C., for several minutes to 24 hours, preferably for 1–10 hours. In order to remove macroscopic aggregates, the fraction can then be centrifuged. Thereafter, the degree of multimerization can be determined by gel permeation chromatography or other common methods. The relative amount of the IgA multimers can be controlled by choosing the appropriate temperature and time of the heating process.

A pharmaceutical preparation according to the invention should be free of anticomplementary activity. This is accomplished by minimizing the content of polymeric IgG. Anti-complementary activity of a composition can be measured with methods according to Kabat and Mayer, EXPERIMENTAL IMMUNOCHEMISTRY (Thomas, Springfield 1961) and Public Health Monograph No. 74: STANDARDIZED DIAGNOSTIC COMPLEMENT FIXATION METHOD AND ADOPTION TO MICROTEST (Washington, 1965) (ch. 4, Complement and Complement Fixation) and estimated to correspond to a value according to which at least 10 mg of protein are necessary for the neutralization of a unit $C'H_{50}$ (the 50% hemolytic unit, defined as the quantity of complement required for 50% lysis). Preferably, at least 35 mg of protein is needed for the neutralization of a unit $CH_{50}$.

Because the IgA administered to the subject will be typically obtained from blood or various fractions thereof, it should be treated to eliminate or inactivate potentially-contaminating pathogens, such as viruses. Procedures for inactivating viruses in blood products are disclosed in EP 0 159 311 and in U.S. application Ser. No. 07/900,164, the entirety of which is hereby incorporated by reference. Other methods of viral inactivation may also be undertaken. Viral-inactivation renders the IgA preparations virus-safe.

As stated above, the IgA preparations of the present invention can be locally or systemically administered. Thus, the IgA-containing preparation can be administered by oral, nasal, intravenous, intraartery, intracavitary, intramuscular, subcutaneous, transdermal, rectal or other routes known to those of skill in the art.

Typically, the IgA is combined with a pharmaceutically acceptable carrier. Such carriers include aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.).

The following examples are intended to further explain the present invention and do not limit the invention in any manner.

EXAMPLE I

Purification of human serum IgA

Purified human serum IgA preparations were prepared by plasma fractionation. First, IgA was purified from serum Cohn fraction II of large plasma pools according to EP 0 506 651. The IgA-enriched preparation was then further purified to obtain a final IgA product that contained more than 95% IgA and no detectable IgG or IgM as examined by single radial immunodiffusion. An IgG preparation, for use in comparative studies, was likewise prepared from serum Cohn fraction II (>97% purity).

Both immunoglobulin preparations were stored in the lyophilized form at 4° C., and all experiments were performed with one lot of the IgA or IgG preparation. Immediately prior to their use in cell cultures the immunoglobulin preparations were dissolved in RPMI 1640 medium (Flow Laboratories, Irvine, UK) supplemented with penicillin (100 IU/ml), streptomycin (100 ug/ml) and Glutamine (2 mM, Gibco, Paisley, Scotland) (RPMI suppl.) containing 1% commercially available human serum albumin (Plasma Protein Fraction Human 3.5% IMMUNO AG, Vienna). This medium is known as "RPMI-HSA".

EXAMPLE II

Preparation of multimeric IgA

Human serum IgA was dissolved at a concentration of 20 mg/ml in RPMI-HSA and aggregated by heating at 63° C. for 20 minutes. The preparation was then centrifuged at 600 x g for 10 minutes to remove macroscopic aggregates.

EXAMPLE III

Preparation of human monocyte monolayers and stimulation of cytokine release

Human mononuclear cells ("MNC") were isolated from heparinized peripheral blood (7.5 IU of preservative free heparin per milliliter) of healthy volunteers by buoyant density gradient centrifugation on Lymphoprep (Nyegaard & Co, Oslo, Norway), according to the method of Bøyum A Scan. J. Clin. Lab. Invest. 21 (Suppl. 97): 77 (1968). The cells from the interphase were aspirated and washed three times in 0.9% NaCl. After the last washing step, the cells were re-suspended at a concentration of $1 \times 10^6$/ml in RPMI suppl. containing 10% pooled, heat inactivated (30 minutes at 56° C.) human AB serum or 10% heat inactivated fetal calf serum (FKS, Flow Laboratories) (complete medium).

For the preparation of monocyte monolayers, one milliliter aliquots of the MNC suspension were pipetted into flat-bottomed 24-well plastic tissue culture plates (Falcon 3047 Multiwell Tissue Culture Plate, Becton Dickinson Labware, Lincoln Park, N.J.). After a 90 minute incubation period at 37° C. in a $CO_2$ incubator (5% $CO_2$ in humidified air), the adherent monocyte monolayers were washed three times with saline to remove non-adherent cells. The adherent cells were then further incubated in complete medium for 24 hours to decrease nonspecific background cytokine production. The cells were then washed three times with 0.15M NaCl, and cytokine release was induced by adding heat-inactivated encapsulated Hib strain Eagan (stock $2 \times 10^9$ bacteria/ml, final concentration $1 \times 10^6$ bacteria/ml) or purified LPS (lipopolysaccharide prepared from E. coli serotype O111:B4 by phenol extraction, obtained from Sigma Chemicals Co., Sigma No L-2630, final concentration 1 ng/ml) to the cell cultures. Five hundred microliters of RPMI-HSA containing Hib ($2 \times 10^6$/ml) or LPS (2 ng/ml) were mixed with 0.5 ml of IgA or IgG in RPMI-HSA at dilutions ranging from 0.2 mg to 20 mg/ml. One milliliter of this mixture was added to a well of the 24-well plastic tissue culture plate containing the adherent monocytes. In selected experiments, the mixture of bacteria and immunoglobulin was preincubated for 30 minutes at 37° C. before addition to the cell cultures. Monocyte cultures set up in the presence of Hib alone, IgA or IgG alone, or medium alone served as controls.

After addition of Hib with or without immunoglobulin to the cells, the adherent monocyte monolayers were incubated for 24 hours at 37° C. in a $CO_2$ incubator. The cell supernatants were then aspirated and centrifuged at 9000 x g for three minutes to remove contaminating cellular material. The cytokine content was determined. If the determination of cytokine content could not be performed on the same day, the supernatants were distributed into aliquots which were kept frozen at −20° C. for a maximum of three days until TNF-α and IL-6 concentrations were measured.

To determine the number of adherent cells per well and the purity of adherent monocytes after 24-hour stimulation with Hib, the adherent cells were gently scraped off. The cells were then centrifuged and the cell number was determined with a Coulter counter. In four experiments, $1.0 \pm 0.3 \times 10^5$ cells per well (mean±SEM of four determinations) could be recovered after 24-hour Hib stimulation. The viability of the cells (as determined by trypan blue exclusion) was 78±5.5%. As examined by flow cytometry using a CD14-specific monoclonal antibody (MO2, Coulter Immunology, Hialeah, Fla.) in direct immunofluorescence, the adherent cells contained 86±4.9% monocytes.

EXAMPLE IV

Examination of cytokine release in monocytes pretreated with Hib

Instead of the 24-hour stimulation of adherent monocytes described above, the cells were stimulated for three hours with Hib in the presence of IgA (10 mg/ml) or Hib only. The monocyte monolayers were then washed twice with saline to remove free Hib, and the cells were subsequently cultured for 21 hours in fresh medium containing IgA (10 mg/ml) or fresh RPMI-HSA alone (medium control). Monocyte supernatants were then collected as described above, and cytokine concentrations were determined by ELISA.

EXAMPLE V

Measurement of TNP-A, IL-6 and GM-CSF in monocyte supernatants

TNF-α, IL-6 and GM-CSF concentrations were determined in monocyte supernatants diluted 1:30 for TNF-α, 1:5 for IL-6 or 1:2 for GM-CSF using commercially available ELISA kits (TNF-α-EASIA and IL-6-EASIA, Medgenix Diagnostics, Fleurus, Belgium and Quantikine Human GM-CSF Immunoassay, R&D Systems, Minneapolis, Minn.). The monoclonal antibodies specific for the respective cytokine used in TNF-α and IL-6 assays are non-neutralizing antibodies that react with an epitope on the cytokine molecule different than the receptor binding site. Consequently, the results from these assays should not be biased by the presence of soluble cytokine receptors or inhibitors. Results are expressed as pg/ml of IL-6, TNF-α or GM-CSF as calculated from a standard curve derived by linear regression of the log-transformed concentrations of the cytokine standards supplied with the ELISA kit versus the respective log-transformed ELISA optical density.

To assess the effect of IgA or IgG on cytokine release, immunoglobulin-induced inhibition is expressed as percentage of control relative to cytokine release observed in cell cultures stimulated with Hib alone in the absence of immunoglobulin (the 100% positive control) or as percent inhibition (that is, 100 - percentage of control). The percentage of control was calculated according to the following formula:

$$\% \text{ of control}=(X-I)/(C-B)\times 100$$

where X is the cytokine concentration of the experimental sample (monocytes plus immunoglobulin plus Hib or LPS), I is the cytokine concentration in the supernatant of monocytes incubated in the presence of immunoglobulin alone, B is the background cytokine release (culture of monocytes alone), and C is the cytokine concentration released from monocytes incubated in the presence of Hib or LPS without immunoglobulin (the 100% control).

EXAMPLE VI

Effect of IgA on TNF-α and IL-6 release in human monocytes

Human monocytes release significant amounts of inflammatory cytokines when triggered by gram negative bacteria such as Hib. The effect of IgA on the Hib-induced release of TNF-α and IL-6 was examined.

Figure 1:
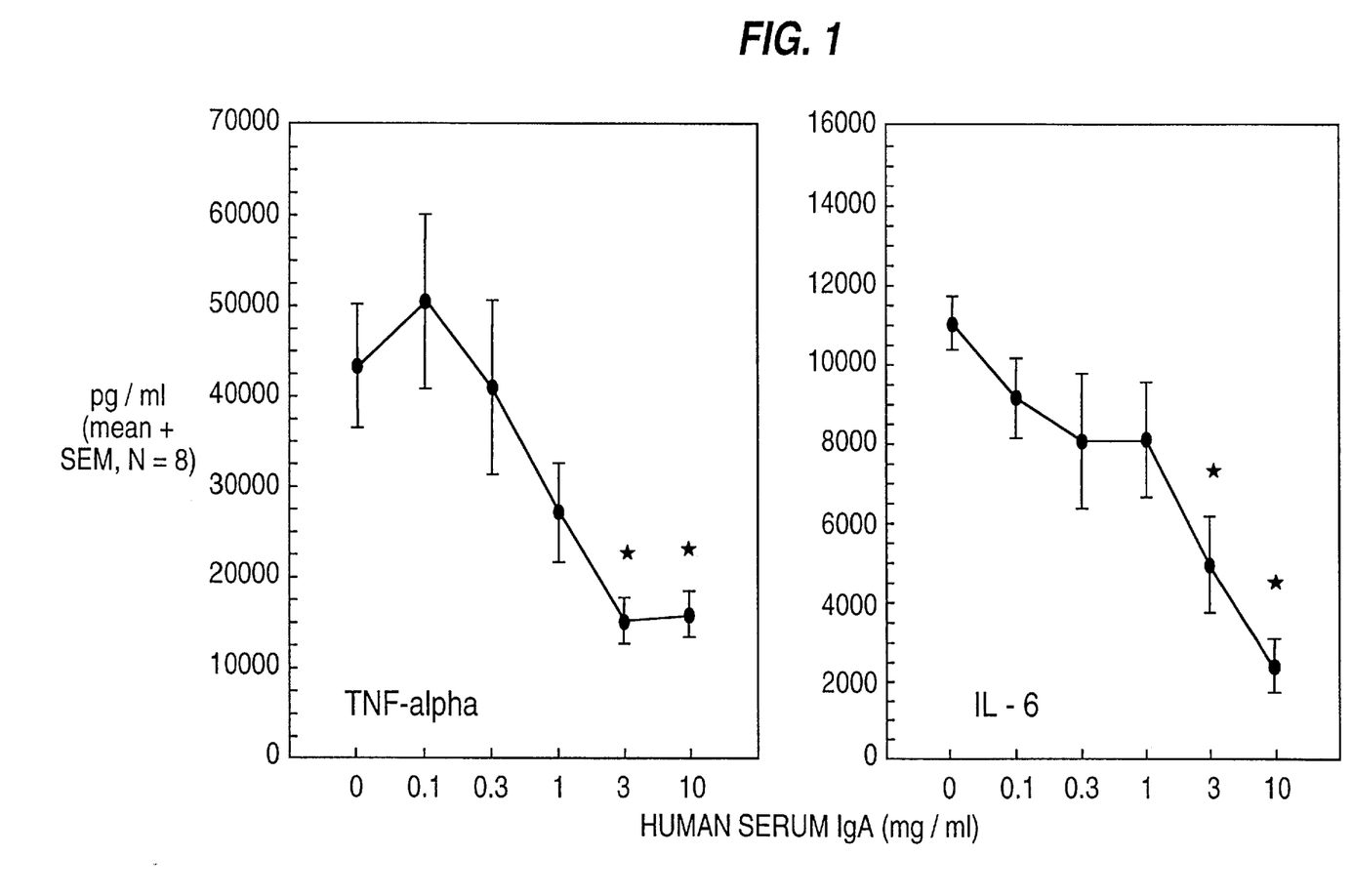
FIG. 1 depicts in graphical form that human serum IgA down-regulates TNF-$\alpha$ and IL-6 release in human monocytes activated with Haemophilus influenza type B.

First, human monocytes were isolated from peripheral blood mononuclear cells by adherence to 24-well plastic tissue culture plates ($1\times10^6$ MNC/well/ml complete medium). The adherent monocytes were stimulated for 24 hours with Hib ($1\times10^6$ bacteria/ml/well) in RPMI-HSA containing human serum IgA at the indicated concentrations. Control wells contained monocytes cultured in the presence of Hib alone. After the 24-hour incubation period, TNF-α and IL-6 concentrations in cell-free supernatants were determined by ELISA. Results are expressed as pg/ml (mean±SEM of 8 individual experiments). Monocytes cultured in medium alone released 18±9 pg/ml of TNF-α and 61±50 pg/ml of IL-6. Background cytokine release in cultures containing IgA only was 31±20 pg/ml (0.1 mg/ml) and 562±263 pg/ml (10 mg/ml) for TNF-α, and 255±148 and 121±82 pg/ml for IL-6.

The data presented in FIG. 1 demonstrates that incubation of monocytes in the presence of Hib ($1\times10^6$ bacteria/ml) under serum-free conditions (in RPMI suppl. containing 1% HSA) induced the release of significant levels of TNF-α (43198±6912 pg/ml) and IL-6 (10990±669 pg/ml). The asterisk ("*") denotes a statistically significant difference between IgA-treated and control cells (p<0.005, Mann-Whitney U test).

Addition of IgA in final concentrations ranging from 0.1 to 10 mg/ml to the cultures of monocytes and Hib resulted in a dose-dependent decrease in the release of both cytokines (FIG. 1). The IgA-mediated inhibition of TNF-α release was maximal at 3 mg/ml (% inhibition, mean±SEM of 8 experiments: TNF-α 65±5, significant difference as compared to cultures with Hib alone was p=0.001636 with the Mann-Whitney U test, and was not enhanced further by increasing the IgA concentration to 10 mg/ml. The effect of IgA on IL-6 release was maximal at 10 mg/ml (81±5% inhibition, p=0.000389), but a statistically significant inhibition by 59±9% could also be observed at 3 mg/ml (p=0.001161).

IgA-mediated inhibition of cytokine release was not due to a reduction in the number of monocytes in the cultures or a decrease in cell viability. As can be seen in Table 1 below, addition of IgA (10 mg/ml) to the cultures had no effect on the number of monocytes per well. Cell viability (as determined by trypan blue exclusion) was also unchanged (data not shown). This indicates that IgA has an effect on the production and/or release of the cytokines of interest.

TABLE 1

| Monocyte treatment | Cytokine release TNF-α | (pg/ml) IL-6 | cells per well ($10^5$) | monocyte purity (%) |
|---|---|---|---|---|
| Medium | 33 ± 20 | 6 ± 6 | 0.8 ± 0.1[1] | 71 ± 8.9[2] |
| IgA[3] | 127 ± 55 | 14 ± 14 | 1.3 ± 0.4 | 78 ± 7.9 |
| Hib | 20553 ± 6272 | 5405 ± 1615 | 1.0 ± 0.3 | 86 ± 4.9 |
| Hib + IgA | 11645 ± 4860[4] | 1313 ± 725[4] | 0.9 ± 0.4 | 80 ± 5.5 |

Values represent mean ± SEM of four experiments.
[1]Cell number was determined with a Coulter counter after detachment of the adherent cells with a rubber policeman.
[2]Determined by flow cytometry with a CD14 mAb in direct immunofluorescence after scraping off the adherent cells.
[3]Human serum IgA was used at 10 mg/ml.
[4]Significant difference as compared to Hib alone (p = 0.0455, Friedman chi-square test for ranks).

Figure 2:
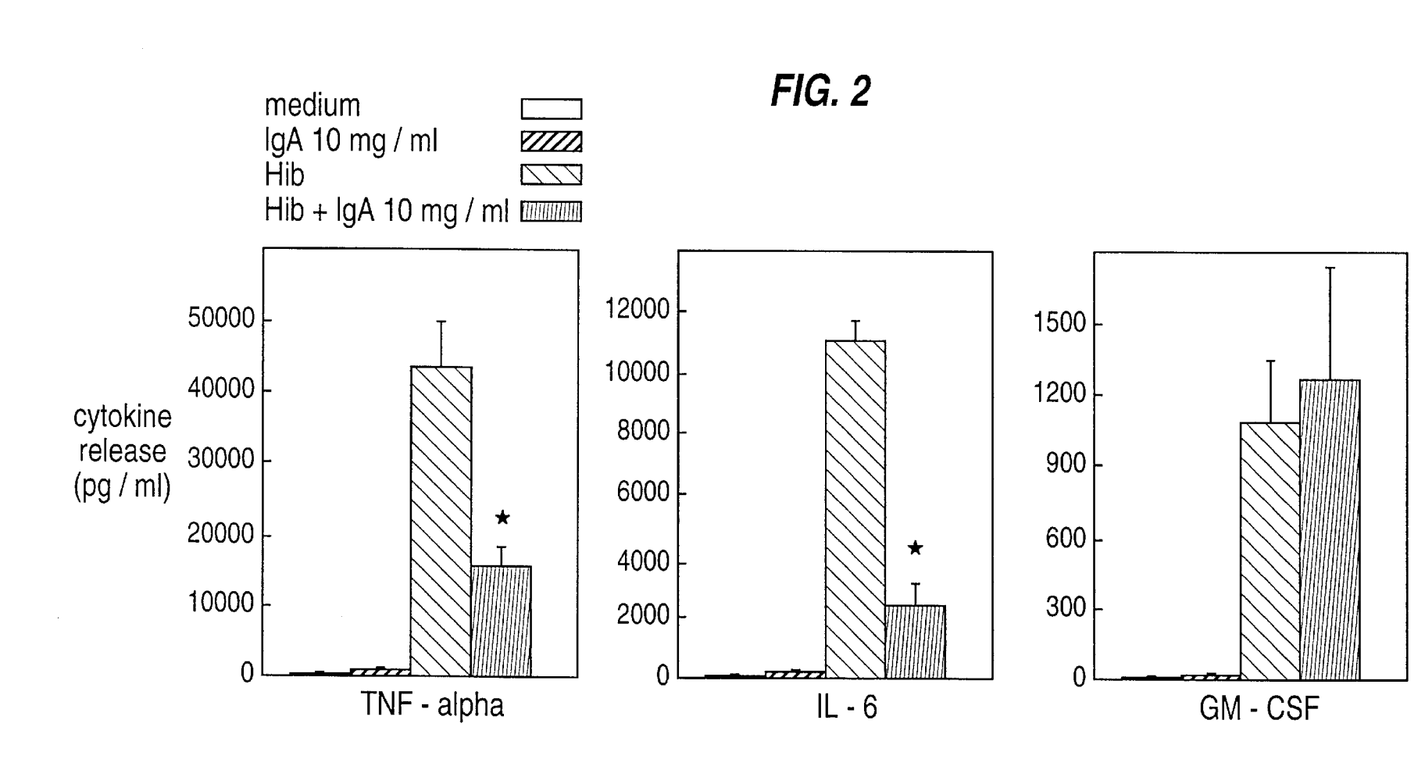
FIG. 2 depicts in graphical form that human serum IgA down-regulates Hib-induced TNF-α and IL-6 release in human monocytes, while GM-CSF production following Hib-stimulation remains unchanged.

FIG. 2 shows that human serum IgA down-regulates Hib-induced TNF-α and IL-6 release in human monocytes, but has no effect on GM-CSF production following Hib-stimulation in this model. First, adherent monocytes were stimulated for 24 hours with Hib in the presence or absence of IgA (10 mg/ml) as was explained for the experiment of FIG. 1. TNF-α, IL-6 and GM-CSF concentrations were determined by ELISA, and results are given as pg/ml (mean±SEM of 8 individual experiments). Background cytokine releases of TNF-α and IL-6 are described in the discussion for FIG. 1. Monocytes cultured in medium alone released no detectable levels of GM-CSF, and only in two of the eight experiments low background GM-CSF release (below 50 pg/ml) was detected in cultures containing IgA (10 mg/ml) without Hib. The asterisk ("*") denotes a statistically significant difference between IgA-treated and control cells (p<0.005, Mann-Whitney U test).

Even high concentrations of IgA (10 mg/ml) had no inhibitory effect on GM-CSF release following Hib-stimulation, while TNF-α and IL-6 release measured in the same supernatants were significantly decreased. Thus, down-modulation of TNF-α and IL-6 release was not due to a generally decreased ability of the monocytes to release cytokines following stimulation with Hib.

The decrease in TNF-α and IL-6 concentration measured in the monocyte supernatants in the presence of IgA was due to a true down-modulation of the release of certain cytokines and not due to inhibition of cytokine detection. The results depicted in Table 2 below show that addition of up to 25 mg/ml of human serum IgA or IgG to supernatant of Hib-activated monocytes had no significant effect on the amount of TNF-α or IL-6 detected, which rules out a possible interference of IgA or IgG antibodies with the measurement of these cytokines by ELISA assays.

TABLE 2

|  |  | cytokine release[1] (pg/ml)[2] | |
|---|---|---|---|
|  |  | TNF-α | IL-6 |
| No antibody | No antibody | 9412 ± 3108 | 3054 ± 1456 |
| IgA | 10 | 9218 ± 3674 | 2744 ± 1622 |
| IgA | 25 | 9187 ± 3579 | 2399 ± 1520 |
| IgG | 10 | 8599 ± 2781 | 2628 ± 1389 |
| IgG | 25 | 9033 ± 3339 | 2386 ± 1499 |

[1]IgG or IgA diluted in RPMI-HSA or RPMI-HSA alone was added to 24-hour supernatants (diluted 1:3 in RPMI-HSA) of Hib-stimulated monocytes.
[2]Values represent mean ± SEM of three independent experiments.

Furthermore, the observed IgA-mediated decrease in TNF-α and IL-6 release was not an artifact due to high protein concentrations in cultures containing IgA. Addition of equivalent amounts of human serum albumin (HSA) to the cultures resulting in a final concentration of 20 mg/ml of HSA had no effect on Hib-induced release of these cytokines. The results were as follows: TNF-α release, pg/ml [% of control]: (i) HSA 10 mg/ml 18540±5678, HSA 20 mg/ml 14922±5040 [84±8%] and (ii) IL-6 release, pg/mil: HSA 10 mg/ml 2426±687, HSA 20 mg/ml 2567±766 [109±10%] (mean±SEM of four experiments).

The IgA-mediated inhibition of Hib-induced TNF-α and IL-6 release was not enhanced by facilitating the interaction of IgA with Hib. The data demonstrated that preincubation of Hib with IgA (10 mg/ml) did not enhance the effect (percent inhibition of cytokine release, mean±SEM: (1) IgA (10 mg/ml) and Hib added to the cells without preincubation (n=8): TNF-α 63±7, IL-6 73±11 and (2) Hib preincubated with IgA for 30 minutes at 37° C. before addition of Hib and IgA to the cells (n=11): TNF-α 59±9, IL-6 51±18).

Figure 3:
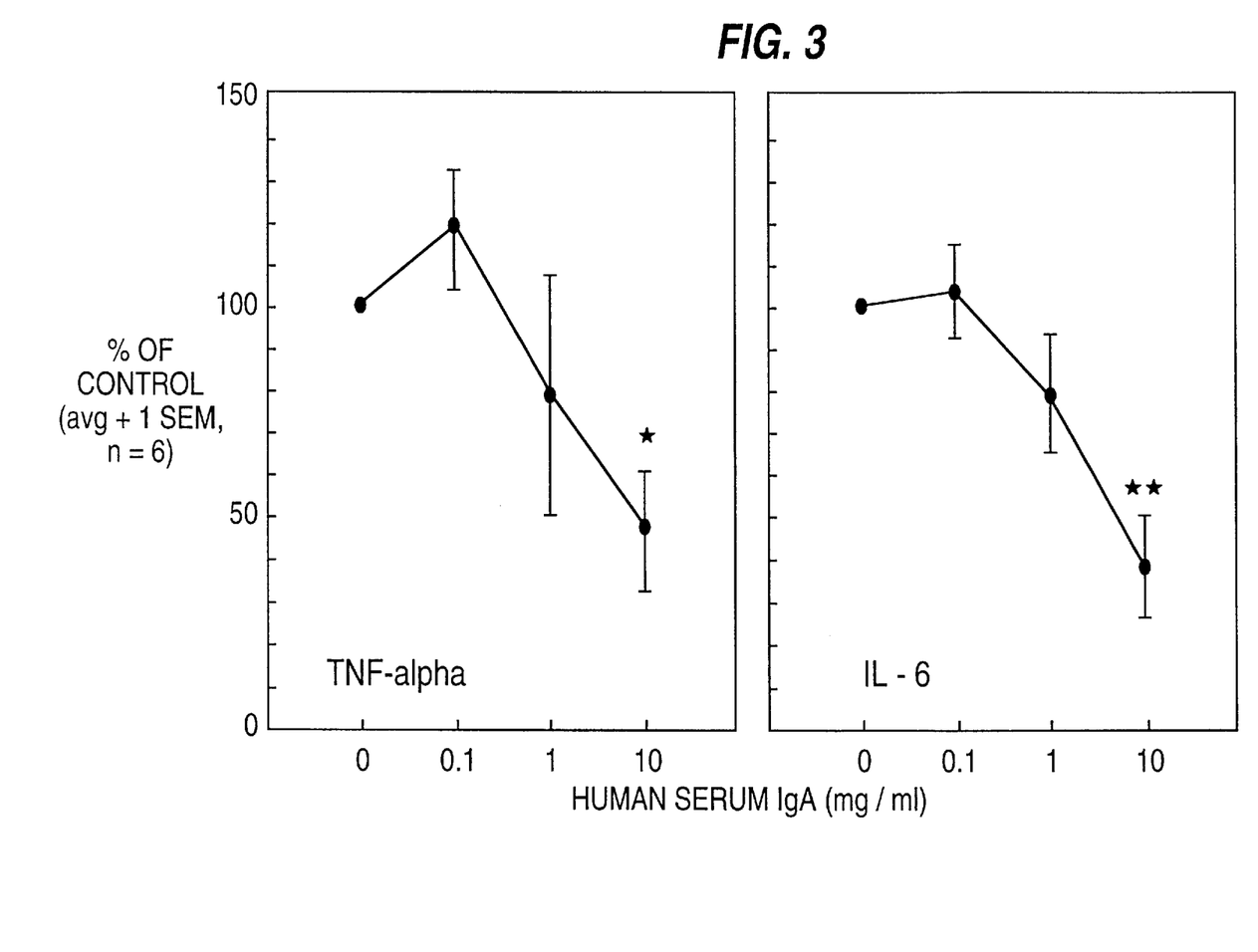
FIG. 3 depicts in graphical form the effect of human serum IgA on TNF-α and IL-6 release in monocytes stimulated with purified LPS.

The experiments depicted in FIG. 3 show that IgA also down-regulates TNF-α and IL-6 release in response to stimulation with a soluble stimulus, LPS purified from *E. coli*. First, adherent monocytes were stimulated for 24 hours with LPS (1 ng/ml) in RPMI-HSA containing human serum IgA (0.1 mg/ml to 10 mg/ml). Control wells contained monocytes and LPS, monocytes and IgA, or monocytes cultured in RPMI-HSA alone. After the 24-hour incubation period, TNF-α and IL-6 release was determined in the cell-free supernatants by ELISA. The results presented in FIG. 3 are expressed as percentage of control cytokine release (cytokines released by monocytes stimulated with LPS in the absence of IgA), calculated as described previously (mean±SEM of six experiments). Control cells stimulated with LPS released 16657±5536 pg/ml of TNF-α and 1110±294 pg/ml of IL-6. Wilcoxon matched-pairs signed-ranks test of the difference in cytokine levels (pg/ml) between IgA-treated and control cultures: p=0.029586, **) p=0.018016.

The results in FIG. 3 shows that the dose response of the IgA-mediated inhibition was comparable for TNF-α and IL-6 release.

EXAMPLE VII

Effect of multimeric IgA on Hib-induced TNF-α and IL-6 release

Figure 4:
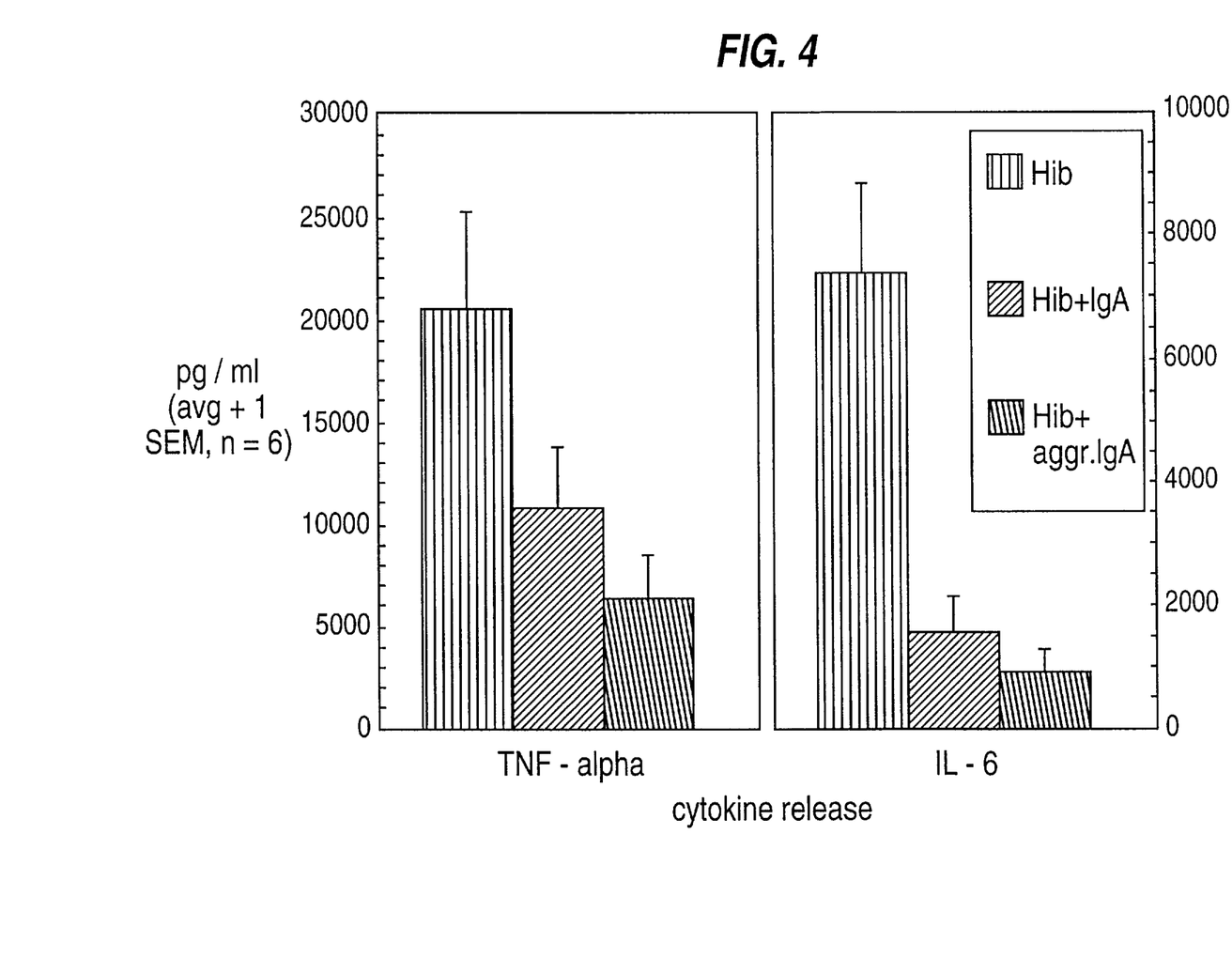
FIG. 4 depicts in graphical form the effect of multimeric (heat-aggregated) and monomeric IgA on cytokine release.

The data in FIG. 4 show that the immunomodulating effect of human serum IgA on TNF-α release is significantly enhanced if IgA is present in a multimeric form.

Human monocytes isolated from peripheral blood mononuclear cells of healthy adult volunteers by adherence to plastic surfaces were cultured in 24-well plastic tissue plates. Adherent monocytes were incubated in the presence of Hib ($1 \times 10^6$ bacteria/ml/well) and monomeric or heat-aggregated IgA (final concentration 10 mg/ml). Control cultures were set up with monocytes and Hib alone. After 24 hours, cell-free supernatants were collected and TNF-α and IL-6 concentrations were determined by ELISA. Results are expressed as pg/ml (mean±SEM of 6 individual experiments).

In six experiments, monomeric IgA reduced TNF-α release by 48±9%, while the inhibition of TNF-α release induced by multimeric IgA (heat-aggregated) in parallel was 73±5% (mean±SEM, n=6, p=0.018686 as compared to % inhibition by monomeric IgA, Mann-Whitney U test). Heat aggregation only slightly enhanced the inhibitory effect of IgA on IL-6 release (% inhibition, mean±SEM: monomeric IgA 78±8%, polymeric IgA 89±3%).

EXAMPLE VIII

Inhibition Studies with IgA and IgG

Figure 5:
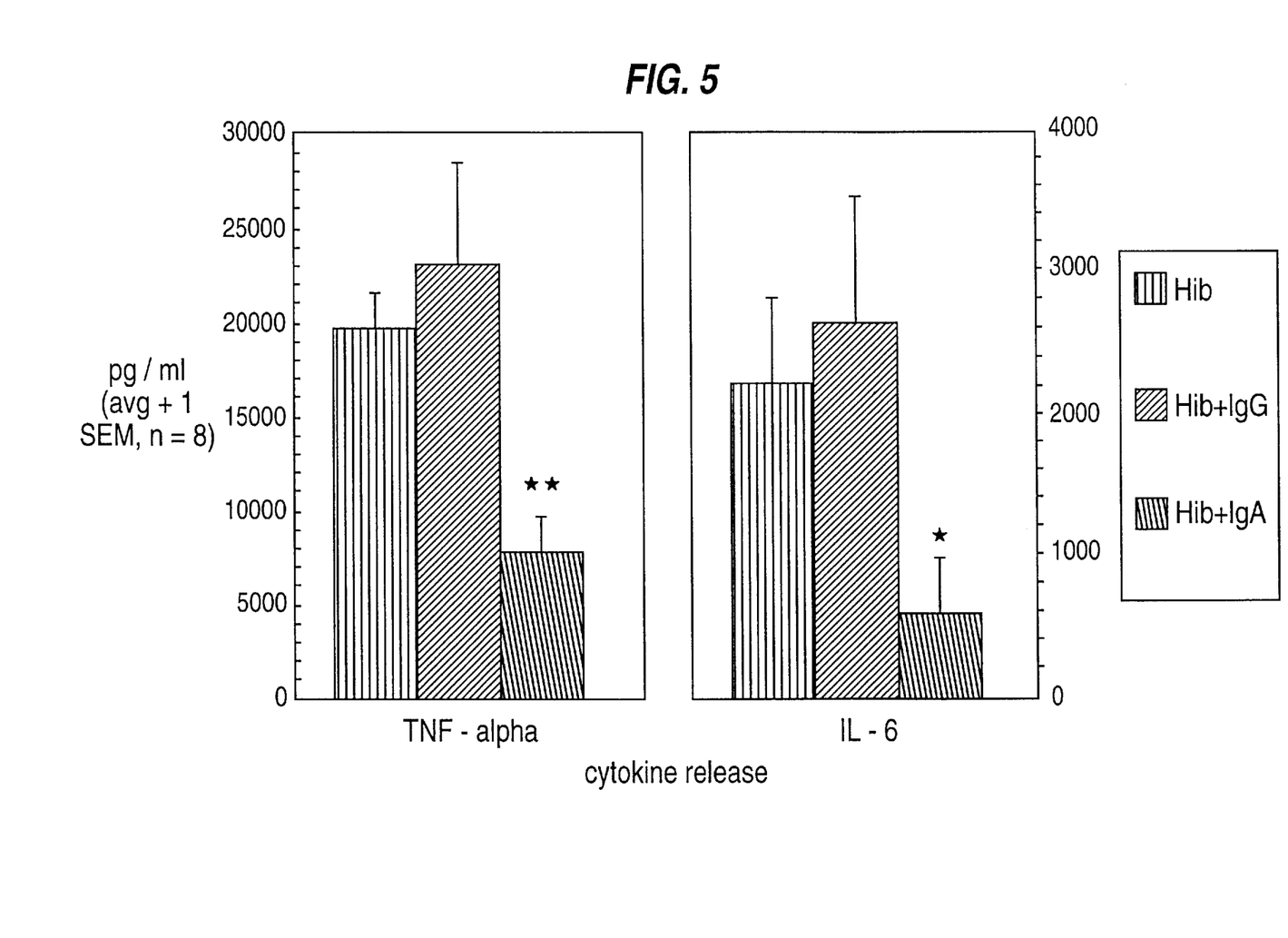
FIG. 5 depicts in graphical form that human serum IgA down regulates TNF-α and IL-6 release in human monocytes, while human serum IgG has no effect.

FIG. 5 shows that IgA significantly reduced the release of TNF-α and IL-6 by adherent monocytes following stimulation with Hib, but IgG examined at a similar concentration had no effect on the levels of cytokine release. First, human monocytes isolated from peripheral blood of healthy volunteers by adherence to plastic were cultured in tissue culture plates (about $1 \times 10^5$ monocytes adhered/well/ml) in the presence of Hib ($1 \times 10^6$ bacteria/ml/well) and IgA or IgG (final concentration 10 mg/ml) for 24 hours. TNF-α and IL-6 levels were then determined in cell-free supernatants by ELISA. Results represent pg/ml (mean±SEM of 8 individual experiments).

Monocytes cultured in the presence of Hib without immunoglobulin served as a positive control, and cells cultured in medium alone without Hib were examined to determine background cytokine release (TNF-α 202±123 pg/ml, IL-6 15±8 pg/ml). Monocytes cultured in the presence of IgG (10 mg/ml) alone released 449±182 pg/ml of TNF-α and 9±5 pg/ml of IL-6; the supernatants of cells treated with IgA (10 mg/ml) alone contained 721±244 pg/ml of TNF-α and 6±2 pg/ml of IL-6. Statistical evaluation of the difference between cytokine release in the presence of IgA or IgG as compared to cells cultured in the presence of Hib alone was performed using the Mann-Whitney U test: * p=0.004326, ** p=0.001638.

EXAMPLE IX

Binding of IgA and IgG to Hib

Figure 6:
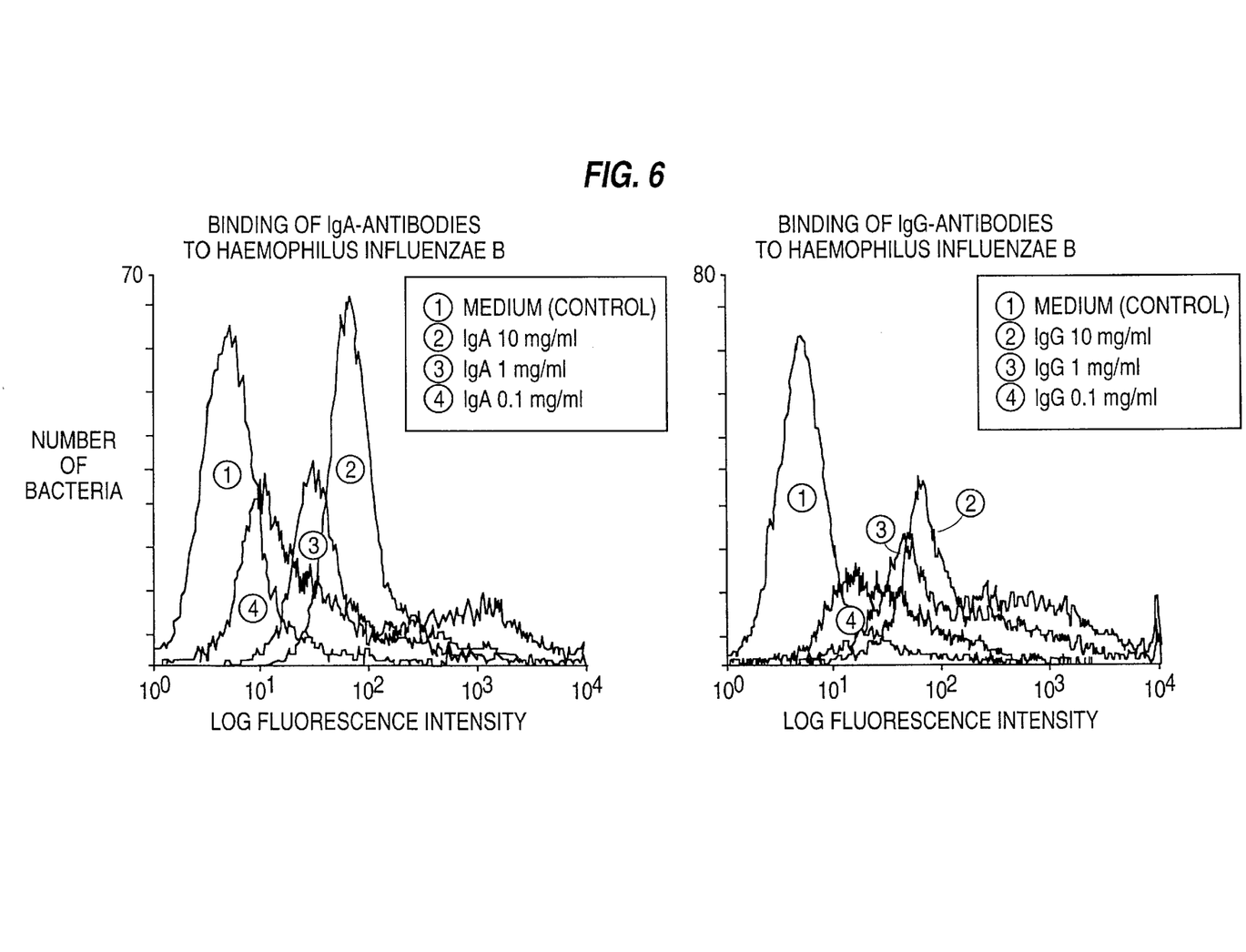
FIG. 6 depicts in graphical form the binding of IgA and IgG antibodies to Haemophilus influenza type B

Because only IgA, and not IgG, down-regulated Hib-induced cytokine release, the binding of IgA and IgG preparations to Hib was investigated. First, Hib was incubated with logfold dilutions of purified human serum IgA or IgG, and the binding of IgA and IgG antibodies was detected by indirect immunofluorescence and evaluated with a cytofluorograph. The medium control represents staining of the bacteria with the FITC-conjugated anti-IgA or anti-IgG reagent alone.

The representative FACS-histograms depicted in FIG. 6 show that both IgA and IgG antibodies bind to Hib, and semiquantitative determinations indicate that both preparations contained comparable titers of Hib-specific antibodies.

EXAMPLE X

Effect of human serum IgA on cytokine induction and cytokine release in monocytes stimulated with Hib There are several possible explanations for the inhibitory effect of IgA on Hib-induced TNF-α and IL-6 release. For instance, IgA could interfere with the Hib-induced stimulation of cytokine release by blocking the binding of Hib to the monocyte surface membrane. This would subsequently lead to decreased levels of cytokine release. The IgA-mediated decrease in Hib-induced TNF-α and IL-6 release could also be the result of a true down-regulation of cytokine production and/or cytokine release in Hib-stimulated monocytes.

Figure 7:
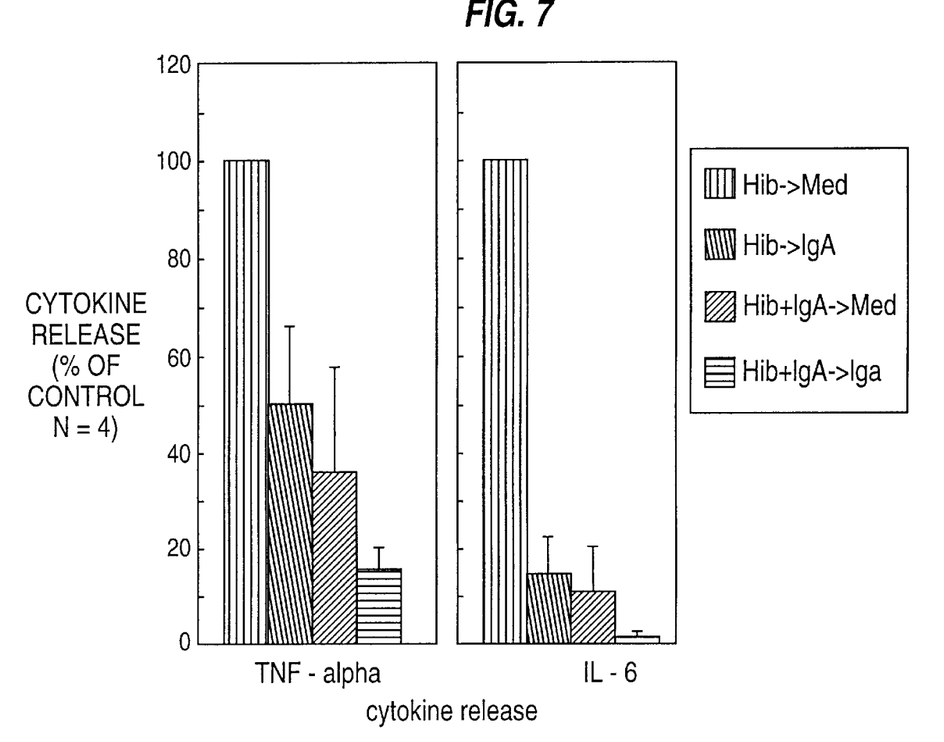
FIG. 7 depicts in graphical form the effect of human serum IgA on cytokine induction and cytokine release in monocytes stimulated with Hib.

The following study was performed to obtain further insights into the anti-inflammatory mechanisms of IgA. Human monocytes were isolated from peripheral blood mononuclear cells ("MNC") by adherence to 24-well plastic tissue plates ($1\times10^6$ MNC/ml/well). Monocyte monolayers were stimulated for 3 hours with Hib ($1\times10^6$ bacteria/ml/well) in RPNI-HSA containing 10 mg/ml of IgA. The adherent monocytes were then washed twice to remove Rib, and were further incubated for 21 hours in fresh medium (RPMI-HSA) containing 10 mg/ml of human serum IgA (Hib+IgA→IgA) or in fresh RPMI-HSA alone (Hib+IgA→Med). Parallel cultures were stimulated for 3 hours with Hib, washed, and then exposed to 10 mg/ml of IgA during the following 21-hour incubation period (Hib→IgA). Cell-free supernatants were collected after the 21-hour incubation following the 3-hour Hib stimulation, and TNF-α and IL-6 concentrations were determined by ELISA. Control cells that were stimulated for 3 hours with Hib, washed, and then cultured for 21 hours in RPMI-HSA without IgA (Hib→Med) released 4939±1588 pg/ml of TNF-α and 1626±728 pg/ml of IL-6. Cytokine release in the IgA-treated cells is expressed as percentage of this control cytokine release, calculated as described above (mean±SEM of 4 individual experiments). Additional wells that were not treated with Hib but had the appropriate media changes and were exposed to IgA or medium alone contained between 65±54 (Med.→IgA) and 113±38 (IgA→IgA) pg/ml of TNF-α and between 8±8 (IgA Med.) and 21±14 (Med.→IgA) pg/ml of IL-6.

Supernatants collected immediately after the 3-hour stimulation with Hib contained only very low amounts of TNF-α (502±178 pg/ml) and IL-6 (288±124 pg/ml, mean±SEM of three experiments), while supernatants collected after a 21-hour incubation following the 3-hour stimulation with Hib (after the stimulus had been removed by extensive washing) contained 3385±463 pg/ml of TNF-α and 1900±953 pg/ml of IL-6, indicating that 88±3% of the total TNF-α and 86±3% of the total IL-6 that is induced by 3-hour stimulation with Hib is released during the 21 hours following stimulation. Continuous stimulation for 24 hours with Hib resulted in 2 to 3 fold higher levels of TNF-α (12849±2904 pg/ml) and IL-6 (4278±766 pg/ml) as compared to the levels of these cytokines in the 21-hour cultures of 3-hour Hib-pretreated monocytes.

As shown in FIG. 7, monocytes stimulated for 3 hours with Hib released markedly reduced levels of TNF-α and IL-6 when IgA (10 mg/ml) was added to the system during the time of cytokine release, after the Hib had been removed by extensive washing (Hib→IgA). In addition, IgA added to the cell cultures during the 3-hour stimulation with Hib also decreased TNF-α and IL-6 release during the 21 hours following stimulation, after IgA and stimulus had been removed by extensive washing (Hib+IgA–Med.).

These results indicate that IgA down-modulates both the induction of cytokine production and cytokine release. If IgA was present both during cytokine induction (the first three hours) and cytokine release in the absence of stimulus (the following 21 hours), the inhibitory effect on TNF-α and IL-6 release was maximal (Hib+IgA→IgA).

In sum, IgA down-regulates the release of TNF-α and IL-6 in activated human monocytes with the particulate stimulus Hib. TNF-α and IL-6 release are down-regulated when IgA is present during the time of continuous stimulation of monocytes with Hib. IgA also inhibits the release of TNF-α and IL-6, if present during cytokine induction. Additionally, IgA is inhibitory if added to Hib-pretreated monocytes after the induction of cytokine production, during the time of cytokine release, even after the stimulus has been removed by extensive washing. When IgA is present both during cytokine induction and cytokine release, the IgA mediated down-regulation of TNF-α and IL-6 production is maximal. This strongly indicates not only a preventive effect of IgA on inflammatory reactions but also a therapeutic effect. Knowledge or accuracy of the proposed mode of action of IgA described above, however, is not necessary for the practice of the present invention.

It is to be understood that the description, tables, figures and specific examples, while indicating preferred embodiments of the invention, are given by way of illustration and are not intended to limit the present invention. Various changes and modifications within the spirit and scope of the invention will become apparent to those skilled in the art from the discussion and data contained herein.

What is claimed is:

1. A method for reducing an inflammatory response, comprising the step of administering a preparation comprising IgA to a subject, wherein the preparation is essentially free of IgG.

2. A method according to claim 1, wherein said preparation is practically free of IgM.

3. A method according to claim 1, wherein said IgA comprises multimeric IgA.

4. A method according to claim 3, wherein said preparation is essentially free of polymeric IgG.

5. A method according to claim 1, further comprising the step of administering a compound selected from the group consisting of antibiotics, antiphlogistic agents and antacids.

6. A treatment method, comprising the step of administering an IgA preparation that is essentially free of IgG to a subject suffering from inflammation, wherein said preparation is administered in an amount sufficient to ameliorate said inflammation.

7. A method according to claim 6, wherein said preparation is practically free of IgM.

8. A method according to claim 6, wherein said IgA comprises multimeric IgA.

9. A method according to claim 8, wherein said preparation is essentially free of polymeric IgG.

10. A method according to claim 6, further comprising the step of administering a compound selected from the group consisting of antibiotics, antiphlogistic agents and antacids.

11. An anti-inflammatory kit comprising:

a preparation comprising IgA in a pharmaceutically acceptable carrier, and a compound selected from the group consisting of antibiotics, antiphlogistic agents and antacids, wherein the preparation is essentially free of IgG.

12. An anti-inflammatory kit according to claim 11, wherein said IgA comprises multimeric IgA.

13. An anti-inflammatory preparation according to claim 11, wherein the preparation comprises multimeric IgA.

14. An anti-inflammatory kit according to claim 11, wherein said preparation is virus-safe.

* * * * *